(12) United States Patent
Gee

(10) Patent No.: US 12,171,930 B2
(45) Date of Patent: Dec. 24, 2024

(54) ERGONOMIC PHACOEMULSIFICATION HANDPIECE

(71) Applicant: Johnson & Johnson Surgical Vision, Inc., Irvine, CA (US)

(72) Inventor: Jacob Gee, Blanchester, OH (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 446 days.

(21) Appl. No.: 17/595,304

(22) PCT Filed: May 15, 2020

(86) PCT No.: PCT/IB2020/054646
§ 371 (c)(1),
(2) Date: Nov. 12, 2021

(87) PCT Pub. No.: WO2020/234730
PCT Pub. Date: Nov. 26, 2020

(65) Prior Publication Data
US 2022/0192879 A1    Jun. 23, 2022

Related U.S. Application Data

(60) Provisional application No. 62/849,792, filed on May 17, 2019.

(51) Int. Cl.
*A61M 1/00* (2006.01)
*A61F 9/007* (2006.01)
(Continued)

(52) U.S. Cl.
CPC ......... *A61M 1/774* (2021.05); *A61F 9/00745* (2013.01); *A61M 3/0283* (2013.01);
(Continued)

(58) Field of Classification Search
CPC ...... A61M 1/774; A61M 1/77; A61M 3/0283; A61M 2210/0612; A61F 9/00745;
(Continued)

(56) References Cited

U.S. PATENT DOCUMENTS 4,180,074 A    12/1979    Murry et al.
4,504,264 A    3/1985    Kelman
(Continued)

FOREIGN PATENT DOCUMENTS

DE    19819432 A1    11/1999
WO    2011008672 A2    1/2011
WO    2019202530 A1    10/2019

*Primary Examiner* — Brooke Labranche
(74) *Attorney, Agent, or Firm* — Johnson & Johnson Surgical Vision, Inc.

(57) ABSTRACT

An apparatus, system and method for a phacoemulsification handpiece. Included are: at least a first segment having a longitudinal axis, and a first end and a second end, wherein at least aspiration, irrigation and power inputs enter the first end; a second segment along the longitudinal axis and comprising, at a distalmost portion thereof from the first segment, a needle powered by the power input, an aspiration output, and an irrigation output; a rotating coupler capable of coupling the second end of the first segment and the second segment to enable independent axial rotation about the longitudinal axis of the first segment from the second segment; and a plurality of flexible tubing passing substantially along the longitudinal axis within both the first segment and the second segment. The plurality of flexible tubing flexes within the first and second segments and within the rotating coupler so as not to bind during the independent axial rotation.

20 Claims, 8 Drawing Sheets

(51) Int. Cl.
*A61M 3/02* (2006.01)
*A61B 17/00* (2006.01)

(52) U.S. Cl.
CPC .............. *A61B 2017/00398* (2013.01); *A61B 2017/0042* (2013.01); *A61B 2017/00424* (2013.01); *A61B 2217/005* (2013.01); *A61B 2217/007* (2013.01); *A61M 1/77* (2021.05)

(58) Field of Classification Search
CPC .. A61B 2017/00398; A61B 2017/0042; A61B 2017/00424; A61B 2217/005; A61B 2217/007
See application file for complete search history.

(56) References Cited

U.S. PATENT DOCUMENTS

| | | | |
|---|---|---|---|
| 5,162,044 | A | 11/1992 | Gahn et al. |
| 5,342,293 | A | 8/1994 | Zanger |
| 5,413,556 | A | 5/1995 | Whittingham |
| 5,453,087 | A | 9/1995 | Malinowski |
| 5,609,602 | A | 3/1997 | Machemer et al. |
| 5,653,724 | A | 8/1997 | Monti |
| 5,843,109 | A | 12/1998 | Mehta et al. |
| 6,086,554 | A | 7/2000 | Humphreys, Jr. et al. |
| D441,863 | S | 5/2001 | Khalaj et al. |
| 6,852,092 | B2 | 2/2005 | Kadziauskas et al. |
| 7,169,123 | B2 | 1/2007 | Kadziauskas et al. |
| D724,726 | S | 3/2015 | Prokop |
| D753,823 | S | 4/2016 | Hayamizu |
| D795,424 | S | 8/2017 | Sloss |
| D870,264 | S | 12/2019 | Fedor et al. |
| D871,574 | S | 12/2019 | Lohk et al. |
| D871,575 | S | 12/2019 | Lohk et al. |
| D871,576 | S | 12/2019 | Lohk et al. |
| D879,290 | S | 3/2020 | Harman et al. |
| D886,999 | S | 6/2020 | Lohk et al. |
| D888,237 | S | 6/2020 | Lohk et al. |
| D898,910 | S | 10/2020 | Hansen et al. |
| D909,575 | S | 2/2021 | Ohno |
| D946,146 | S | 3/2022 | Gee et al. |
| 2001/0018570 | A1 | 8/2001 | Sussman et al. |
| 2005/0277970 | A1 | 12/2005 | Norman et al. |
| 2006/0079832 | A1 | 4/2006 | Akahoshi |
| 2008/0161720 | A1 | 7/2008 | Nicoson et al. |
| 2008/0294087 | A1 | 11/2008 | Steen et al. |
| 2009/0005712 | A1 | 1/2009 | Raney |
| 2010/0069825 | A1 | 3/2010 | Raney |
| 2010/0228119 | A1 | 9/2010 | Brennan et al. |
| 2011/0009874 | A1 | 1/2011 | Wardle et al. |
| 2011/0137231 | A1 | 6/2011 | Sorensen et al. |
| 2012/0078234 | A1 | 3/2012 | Merchant, I et al. |
| 2014/0276369 | A1* | 9/2014 | Banko .................. A61M 1/774 604/22 |
| 2015/0133946 | A1 | 5/2015 | Horvath et al. |
| 2016/0038342 | A1 | 2/2016 | Van et al. |
| 2018/0333165 | A1 | 11/2018 | Algawi et al. |
| 2019/0321017 | A1 | 10/2019 | Christopher et al. |
| 2021/0007891 | A1 | 1/2021 | Gee |
| 2021/0100574 | A1 | 4/2021 | Magno |
| 2022/0096270 | A1 | 3/2022 | Brady |

* cited by examiner

ERGONOMIC PHACOEMULSIFICATION HANDPIECE

CROSS-REFERENCE TO RELATED APPLICATIONS

This application is a U.S. national stage of and claims the benefit under 35 U.S.C. § 371 of International Patent Application No. PCT/IB2020/054646, filed May 15, 2020, which claims priority to U.S. Provisional Patent Application No. 62/849,792, filed on May 17, 2019, the entire contents of which are hereby incorporated by reference in their entirety.

FIELD OF THE DISCLOSURE

The field of the invention relates to a handpiece, and more particularly to an apparatus, system and method for ergonomic phacoemulsification handpieces.

BACKGROUND OF THE DISCLOSURE

The phacoemulsification method includes emulsifying, or liquefying, the cataractic lens with an ultrasonically driven needle before the lens is aspirated. A phacoemulsification system 5 known in the art is shown in FIG. 1. The system 5 generally includes a phacoemulsification handpiece 10 coupled to an irrigation source 30 and more or more aspiration pumps, e.g. pump 40.

The handpiece 10 includes a distal tip (or needle) 15 (shown within the anterior chamber of the patient's eye 1) that emits ultrasonic energy to emulsify the cataractic lens within the patient's eye 1. The handpiece 10 further includes a sleeve 26 that surrounds at least a portion of needle 15, and which provides one or more irrigation ports 25 proximal to the distal tip 15 that are coupled to an irrigation source 30 via an irrigation line 35, and an aspiration port 20 at the distal tip 15 which is coupled to aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirated from the eye 1 by the aspiration pump 40 via the aspiration port 20 and the aspiration line 45.

Turning to FIG. 2, a functional block diagram of a phacoemulsification system 100 known in the art is shown. The system 100 includes a control unit 102 and a handpiece 104 operably coupled together. The control unit 102 generally controls the operating parameters of the handpiece 104, e.g., the rate of aspiration A, rate of irrigation (or flow) F, and power P applied to the needle, and hence the eye E. The control unit 102 generally includes a microprocessor computer 110 which is operably connected to and controls the various other elements of the system 100.

The control unit 102 may include an aspiration pump, such as a Venturi (or vacuum-based pump) or a variable speed pump (or a flow based or peristaltic pump) 112, for providing a vacuum/aspiration source, which, in the case of a variable speed pump 112, can be controlled by a pump speed controller 116. The unit 102 further includes an ultrasonic power source 114 and an ultrasonic power level controller 118 for controlling the power P applied to the needle of the handpiece 104. A vacuum sensor 120 provides an input to the computer 110 representing the vacuum level on the output side of the pump 112. Venting may be provided by a vent 122.

The system 100 may also include a phase detector 124 for providing an input to the computer 100 that represents the phase between a sine wave representation of the voltage applied to the handpiece 104 and the resultant current into the handpiece 104. Further disclosure about the phase detector 124 can be found in U.S. Pat. No. 7,169,123 to Kadziauskas et al., which is incorporated herein in its entirety by reference. The functional representation of the system 100 also includes a system bus 126 to enable the various elements to be operably in communication with each other.

Turning to FIG. 3, the cross-section along the longitudinal axis of a portion of a phacoemulsification handpiece 200 known in the art is shown. Generally, the handpiece 200 includes a needle 210, defining a lumen that is operatively coupled to an aspiration pump (e.g. aspiration pump 40 (FIG. 1)), forming an aspiration line 214. At least a portion of the distal end of needle 210 is surrounded by sleeve 220 and proximal end of the needle 210 is coupled to a horn 250, which has its proximal end coupled to a set of piezoelectric crystals 280, shown as three rings. The horn 250, crystals 280, and a proximal portion of the needle 210 are enclosed within a handpiece casing 270 having an irrigation port coupled to an irrigation line 290 defining an irrigation pathway 295. Irrigation pathway 295 extends between the wall of sleeve 220 and the wall of needle 210, allowing fluid to flow around needle 210 and exit one or more ports 225 in sleeve 220. The irrigation line 290 is coupled to the irrigation source 30 (FIG. 1).

The horn 250 is typically an integrated metal, such as titanium, structure and often includes a rubber O-ring 260 around the mid-section, just before the horn 250 tapers to fit with the needle 210 at the horn's 250 distal end. The O-ring 260 snugly fits between the horn 250 and the casing 270. The O-ring 260 seals the proximal portion of the horn 250 from the irrigation pathway 295. Thus, there is a channel of air defined between the horn 250 and the casing 270. Descriptions of handpieces known in the art are provided in U.S. Pat. No. 6,852,092 (to Kadziauskas et al.) and U.S. Pat. No. 5,843,109 (to Mehta et al.), which are hereby incorporated by reference in their entirety.

In preparation for operation, a sleeve 220 is typically added to the distal end of the handpiece 200, covering the proximal portion of the needle 210 (thus, exposing the distal tip of the needle), and the distal end of the irrigation pathway 295, thereby extending the pathway 295 and defining an irrigation port 222 and/or port 225 just before the distal tip of the needle 210. The needle 210 and a portion of the sleeve 220 are then inserted through the cornea of the eye to reach the cataractic lens.

During operation, the irrigation path 295, the eye's chamber and the aspiration line 214 form a fluidic circuit, where irrigation fluid enters the eye's chamber via the irrigation path 295, and is then aspirated through the aspiration line 214 along with other materials that the surgeon desires to aspirate out, such as the cataractic lens. If, however, the materials, such as the cararactic lens, are too hard and massive to be aspirated through the aspiration line 214, then the distal end of the needle 210 is ultrasonically vibrated and applied to the material to be emulsified into a size and state that can be successfully aspirated.

The needle 210 is ultrasonically vibrated by applying electric power to the piezoelectric crystals 280, which in turn, cause the horn 250 to ultrasonically vibrate, which in turn, ultrasonically vibrates the needle 210. The electric power is defined by a number of parameters, such as signal frequency and amplitude, and if the power is applied in pulses, then the parameters can further include pulse width, shape, size, duty cycle, amplitude, and so on. These parameters are controlled by the control unit 102 and example control of these parameters is described in U.S. Pat. No. 7,169,123 to Kadziauskas et al.

With respect to FIG. 4, an exemplary handpiece known in the prior art is shown. As discussed above, the distal end 401 of the handpiece 400 is show with a tip/needle 404 and sleeve 403 having port 405. The proximal end 402 of the of the handpiece 400 comprises multiple ports/connector points 406, include a port 406a for connecting to the irrigation line, a port 406b for connecting to the aspiration line, and a connector port 406c for electrical power for the ultrasound.

The location of the ports/connector points 406 at the proximal end 402 of the handpiece 400 are known to create fatigue on the surgeon's hand and wrist due to the invariability in the orientation of the ports/connector points 406 in light of the rigidly correspondent weight of the proximal end 402 once the irrigation and aspiration lines and the power cord are connected to the handpiece (not shown). This fatigue from orienting the distal end of the handpiece results, in part and as shown in FIG. 4, from the typical construction of the handpiece as one piece metal-type material. Consequently, to adjust or rotate the distal end of the phacoemulsification (phaco) tip/needle requires the entire handpiece and connected lines to be moved/rotated in unison to achieve the desired position. This need to move/rotate the entire handpiece creates the aforementioned fatigue to the surgeon's hand and/or wrist during surgery. As such, a new handpiece with features that address these drawbacks is needed.

SUMMARY

The disclosure is and includes an apparatus, system and method for a phacoemulsification handpiece. The apparatus, system and method may include at least a first segment having a longitudinal axis, and a first end and a second end, wherein at least aspiration, irrigation and power inputs enter the first end; a second segment along the longitudinal axis and comprising, at a distalmost portion thereof from the first segment, a phacoemulsification needle powered by the power input, an aspiration output, and an irrigation output; a rotating coupler capable of coupling the second end of the first segment and the second segment to enable independent axial rotation about the longitudinal axis of the first segment from the second segment; and a plurality of flexible tubing passing substantially along the longitudinal axis within both the first segment and the second segment. At least a first flexible tube of the plurality may provide continuous fluidic communication between the aspiration input and the aspiration output, and at least a second flexible tube of the plurality may provide continuous fluidic communication between the irrigation input and the irrigation output. The plurality of flexible tubing flexes within the first and second segments and within the rotating coupler so as not to bind during the independent axial rotation.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the disclosure. Moreover, in the figures, like reference numerals may designate corresponding parts throughout the different views. However, like parts may not always have like reference numerals. Moreover, all illustrations are intended to convey concepts, where relative sizes, shapes and other detailed attributes may be illustrated schematically rather than literally or precisely.

DETAILED DESCRIPTION

Figure 1:
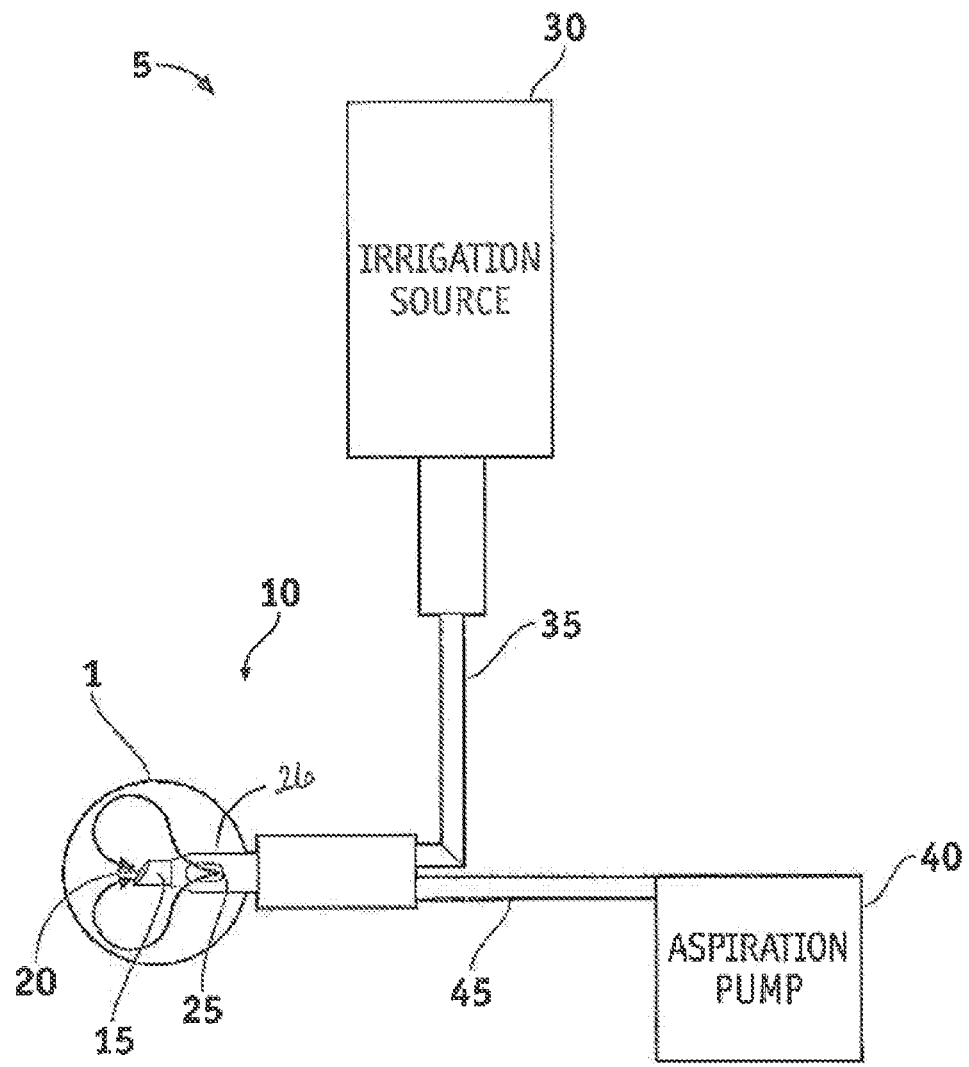
FIG. 1 is a diagram of a phacoemulsification system known in the art.
Figure 2:
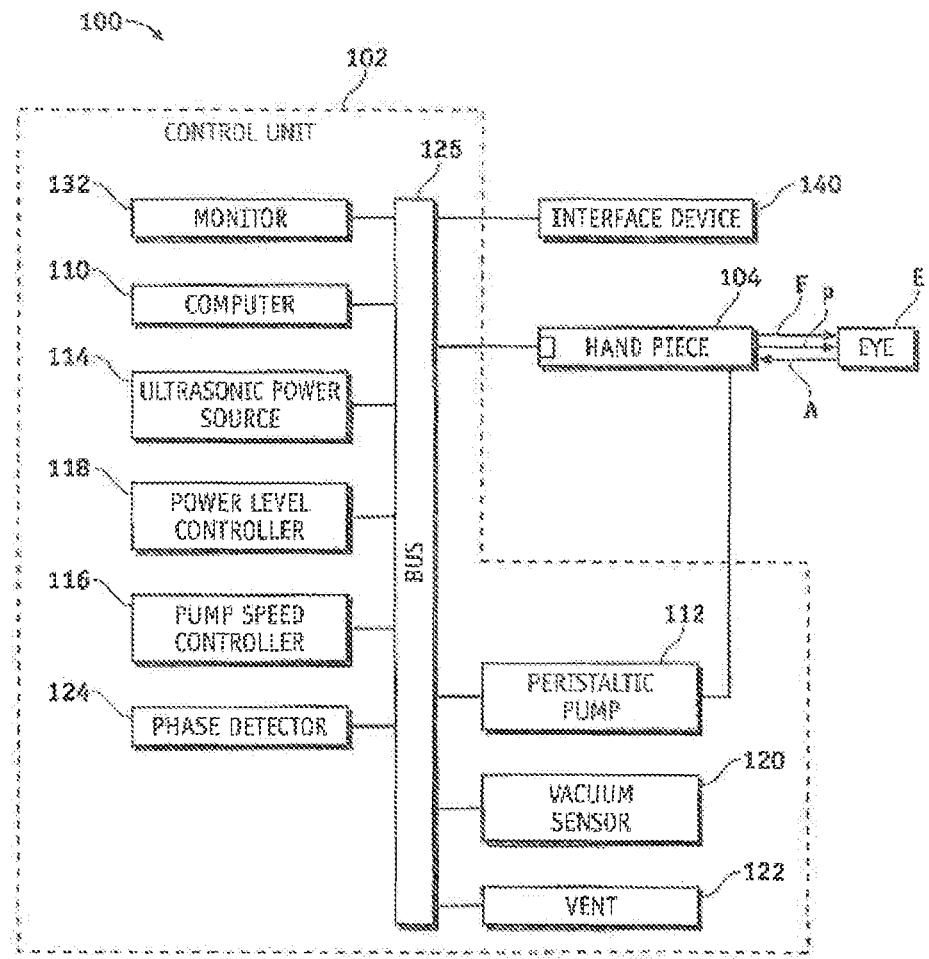
FIG. 2 is another diagram of a phacoemulsification system known in the art.
Figure 3:
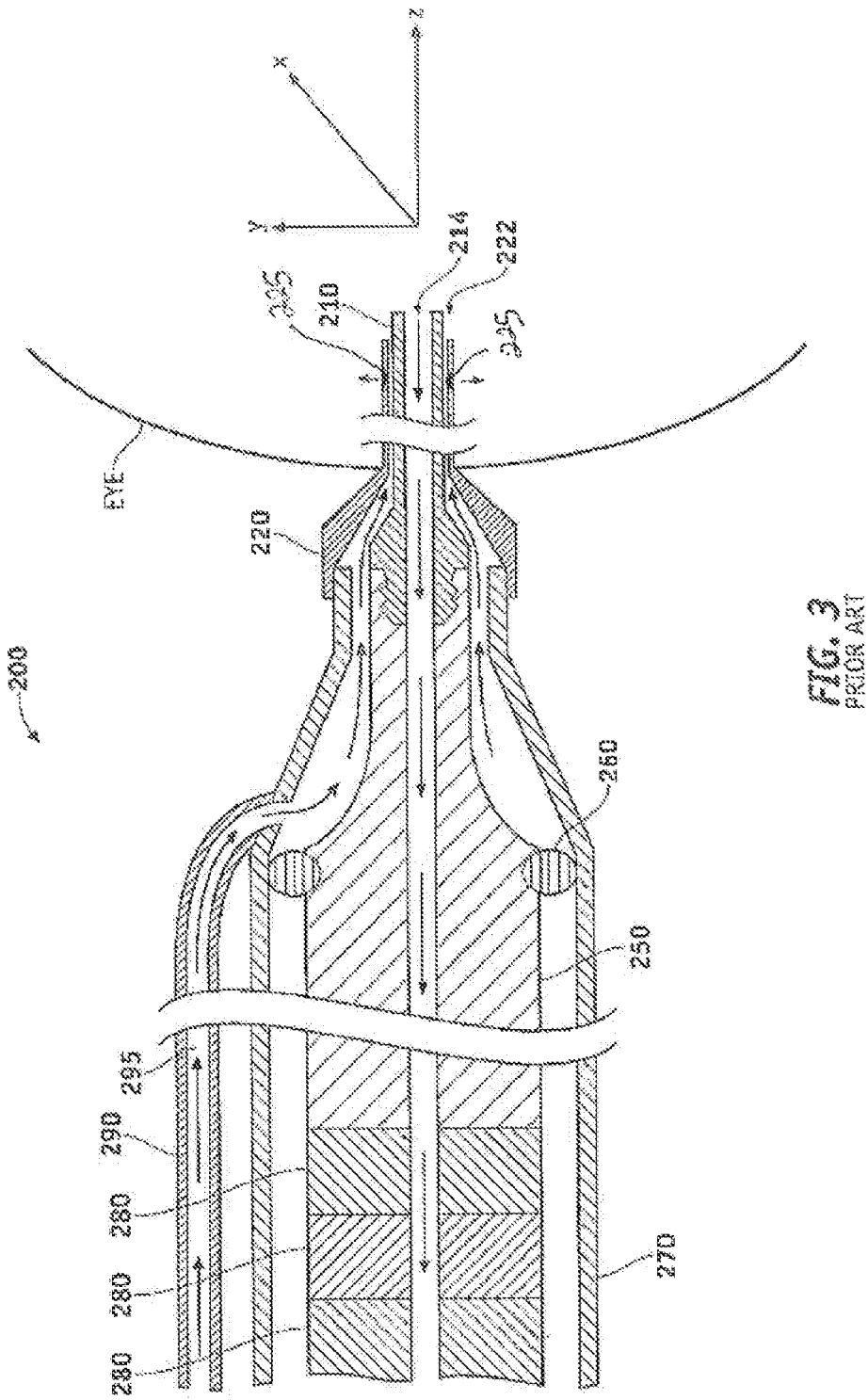
FIG. 3 is a diagram of a phacoemulsification handpiece known in the art.
Figure 4:
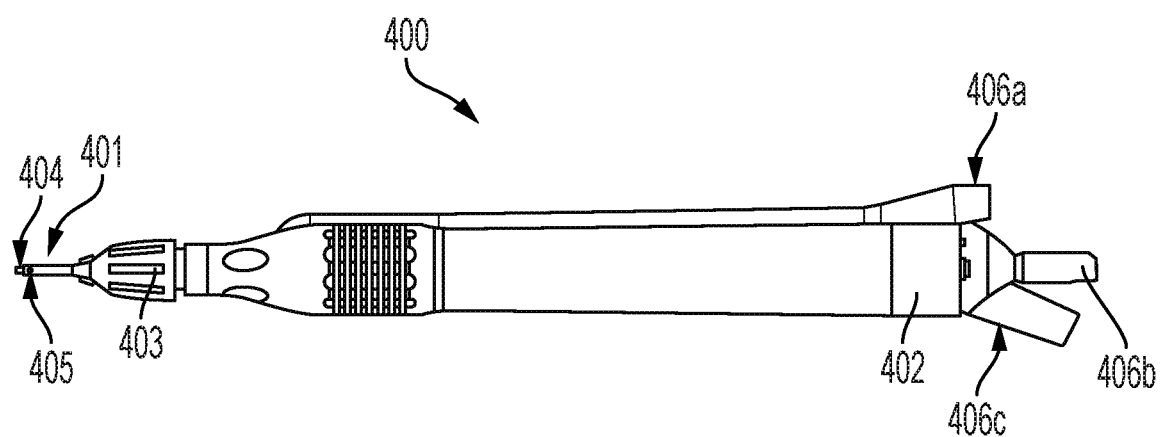
FIG. 4 is an example of a phacoemulsification handpiece known in the art.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical surgical, and particularly ophthalmic surgical, devices, systems, and methods. Those of ordinary skill may thus recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements or aspects, these elements or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, component, region, layer or section discussed below could be termed a second element, component, region, layer or section without departing from the teachings of the disclosure.

The present disclosure relates to ergonomic handpieces, and in particular to a handpiece that has one or more rotatable segments in conjunction with managed, twistable cords and irrigation/aspiration lines, which allows for rotation of the phacoemulsification tip independent of these cords and lines. Thereby, surgeon fatigue is relieved.

Figure 5A:
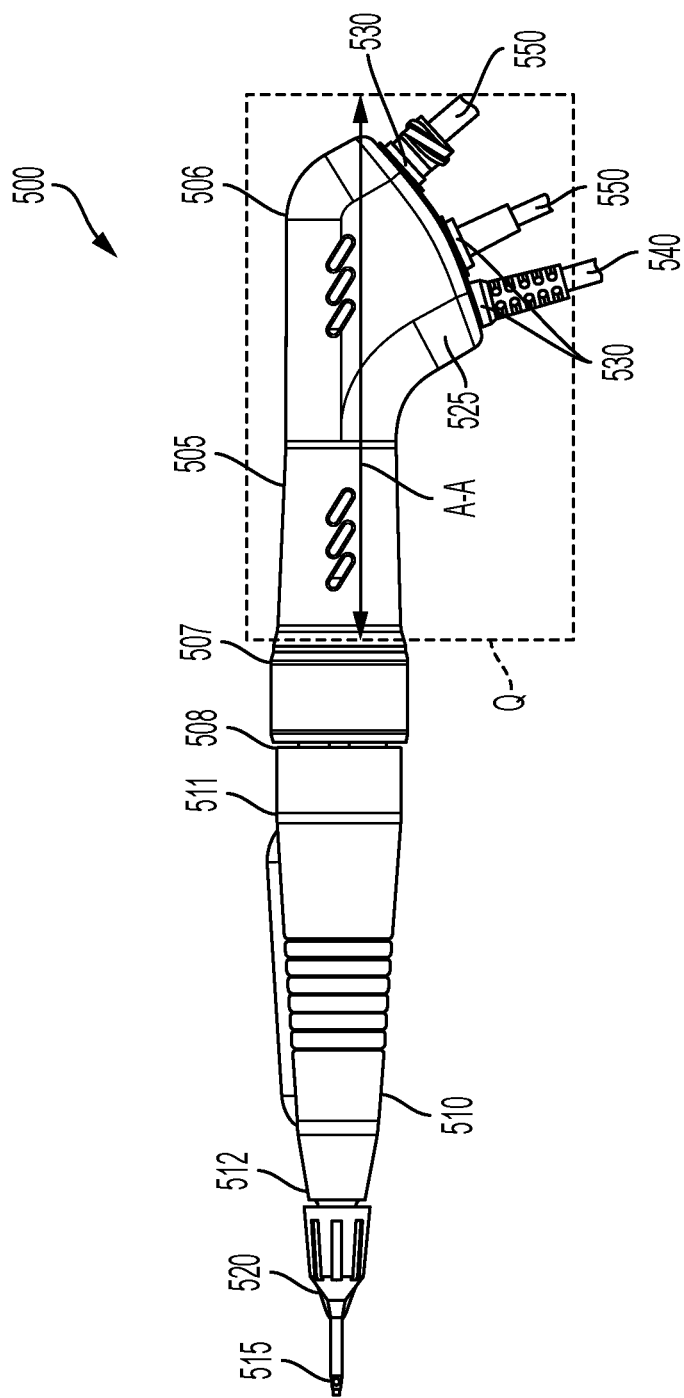
FIGS. 5A and 5B show an embodiment of a handpiece of the present disclosure.
Figure 5B:
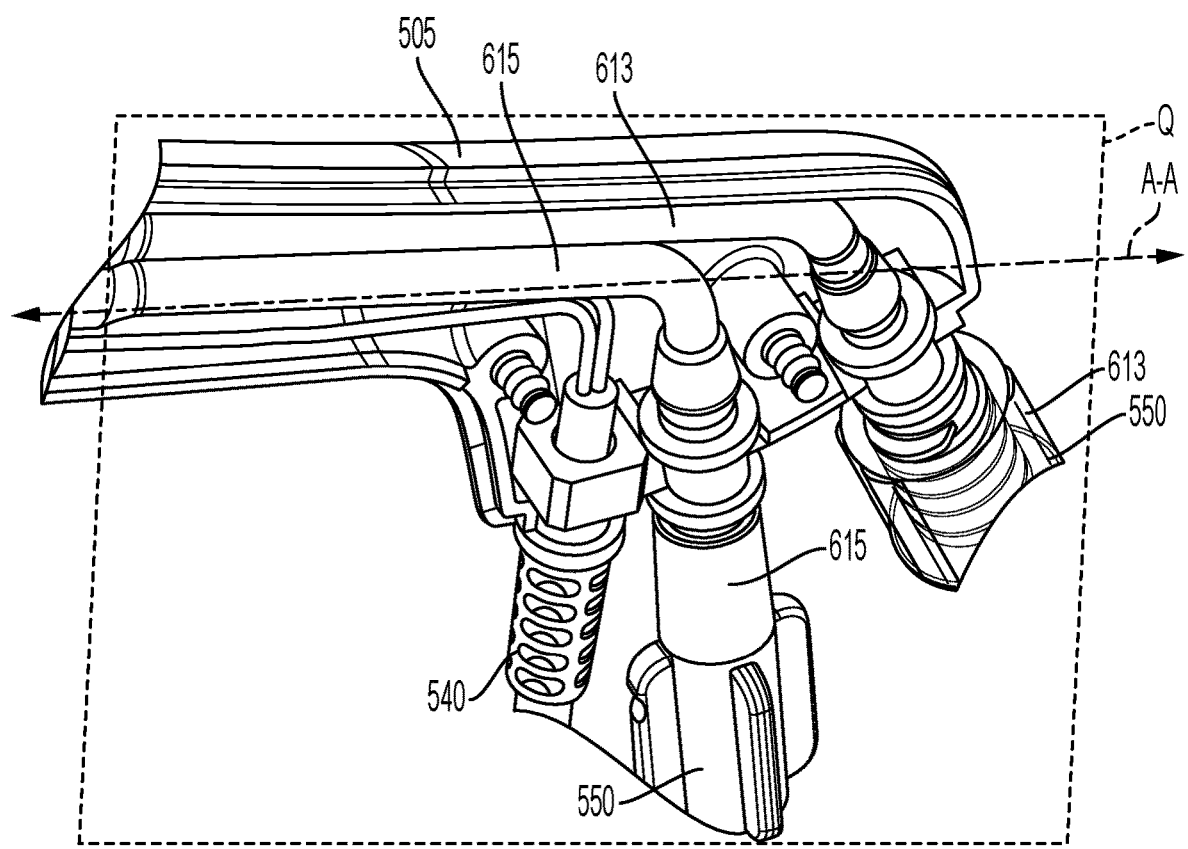

In an embodiment, as shown in FIGS. 5A and 5B, the handpiece 500 may have at least two segments, a proximal segment 505 and a distal segment 510. Proximal segment 505 and distal segment 510 may be coupled to each other. Proximal segment 505 may have a first end 506 and a second end 507. Distal segment 510 may have a first end 511 and a second end 512. Proximal segment 505 may be coupled to distal segment 510 via the first end 511 and second end 507. Proximal segment 505 and second segment 510 may be coupled together by coupler 508 using any means known in the art, including, but not limited to a low friction stainless steel bearing that freely allows axial rotation between the proximal segment 505 and the distal segment 510, such as axial rotation up to 350 degrees. In an embodiment, the axial rotation may be up to 180 degrees. In another embodiment, the axial rotation may be up to 90 degrees.

The coupler 508 may reside between the first end 511 and the second end 507. In addition, the at least one coupler 508 may be a part of the proximal segment 505 or the distal segment 510, and provides a swivel feature that allows proximal segment 505 and distal segment 510 to rotate independently of one another about an axis A. In an embodiment, the proximal and/or distal segments may be capable of rotating up to 359 degrees. In another embodiment, the rotation may be limited to more substantially less than 360 degrees depending upon the freedom of movement desired and the tubing and cabling capabilities, as discussed below. In embodiments, the material of the coupler may be the same as the segment it is connected to, or may be of a different material as referenced above.

In an embodiment, the distal segment 510 of handpiece 500 may have a needle 515 connected to a distal-most portion of distal segment 510. A sleeve 520 may also be coupled with handpiece 500 and at least partially surround needle 515. Needle 515 and sleeve 520 may be separate components attachable to the distal segment 510 or may be integrally coupled with the distal segment 510 of handpiece 500. Proximal segment 505 of handpiece 500 includes tubing/cord management section 525 that includes one or more port/connector 530.

The one or more port/connector 530 has cords 540 and/or tubing 550 connected thereto. In the known art, these connected cords 540 and/or tubing 550 lays or rests against a user's hand or wrist as the distal segment 510 is moved about.

According to an embodiment, a user's hand may grip the distal segment 510, such as between the thumb and pointer finger. This positioning, coupled with a swivel connector 508, allows the user to rotate the distal segment 510 independent of proximal segment 505. That is, proximal segment 505 may remain partially or substantially stationary while distal end 505 is rotatably moved about.

FIG. 5B illustrates a cross-section, along axis A-A, of handpiece portion "Q" of FIG. 5A. More specifically, FIG. 5B illustrates aspiration 615 and irrigation 613, from the input tubes 550 for both toward the distal segment 510. Also shown electrically associated with cord 540 is power into proximal end 505.

Figure 6A:
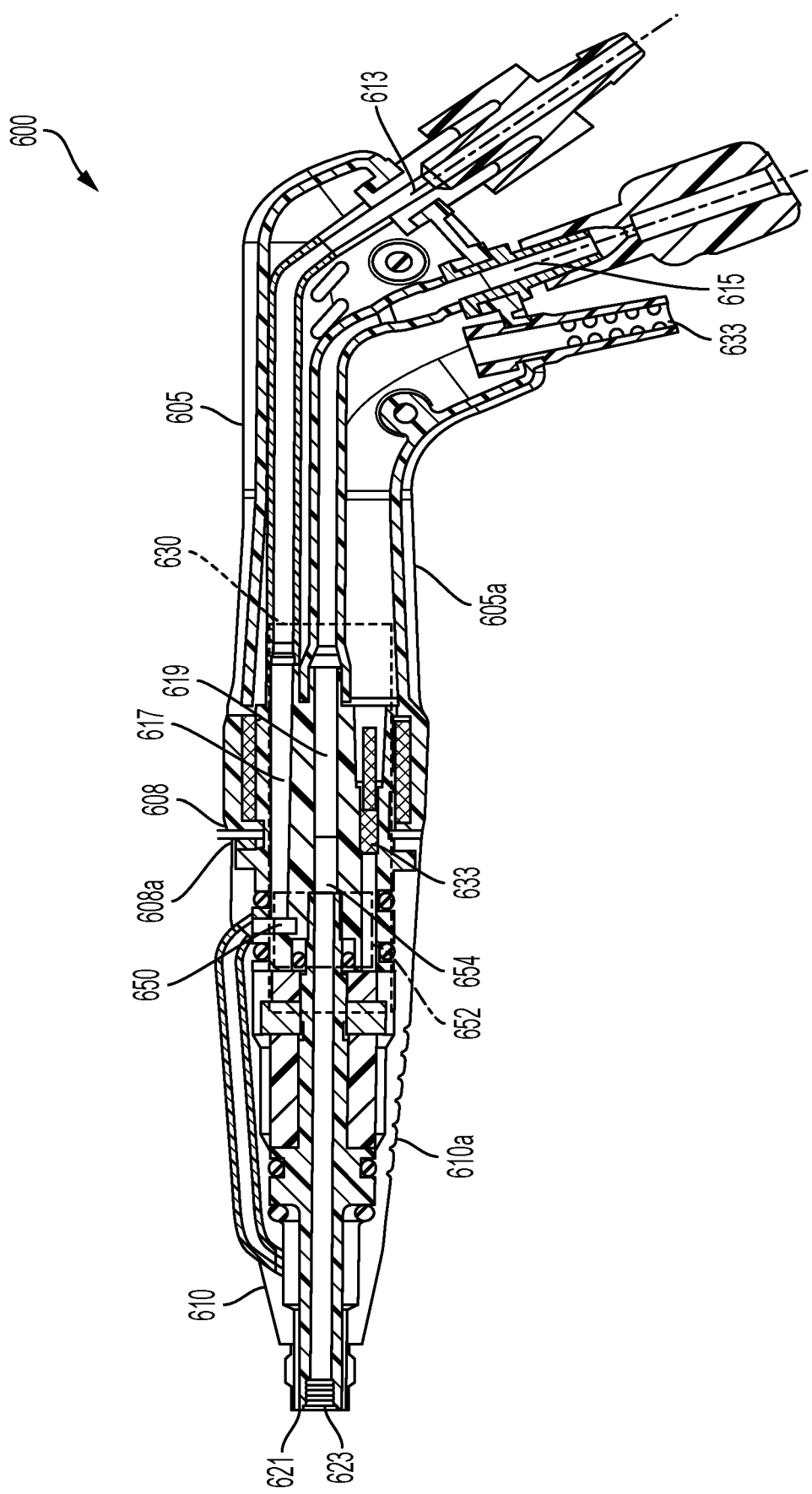
FIGS. 6A and 6B show an embodiment of a handpiece of the present disclosure.
Figure 6B:
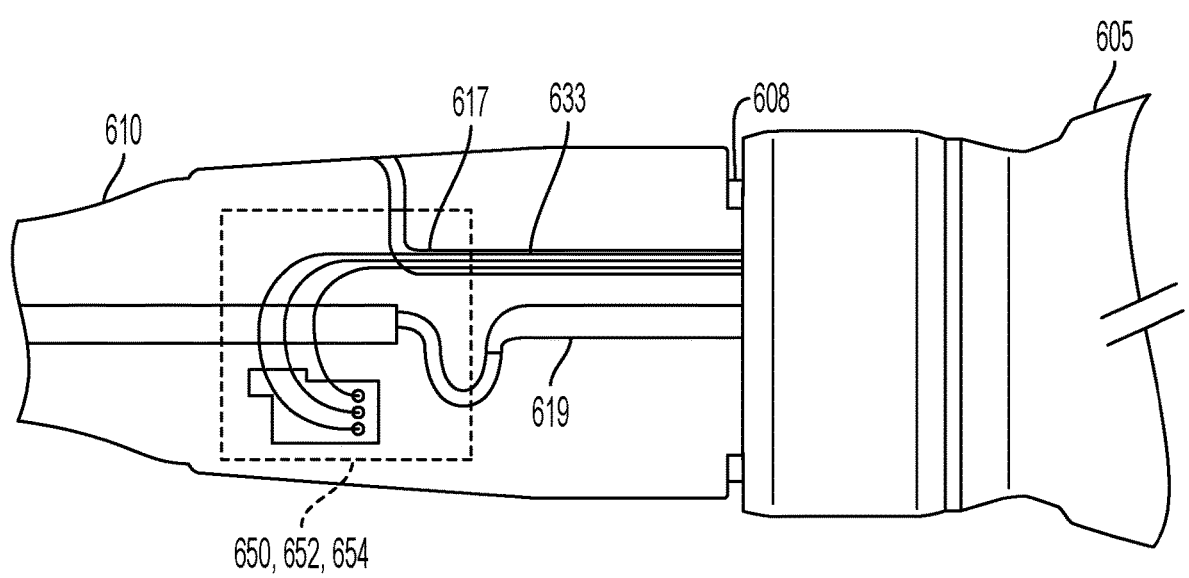

A handpiece 600 is shown in the cross-sectional illustrations of FIGS. 6A and 6B. As shown, the handpiece includes a proximal portion 605 and a distal portion 610, which are free to rotate axially about a coupler 608.

Fluidically connected at the proximal end 605 are the inputs for irrigation 613 and aspiration 615, which are output/ported at the distal end 610. The irrigation and aspiration provided at proximal end inputs 613 and 615 are carried to the distal end via at least one internal irrigation tube 617 and at least one internal aspiration tube 619. Of note, although continuous fluidic communication is thereby provided by internal tubes 617, 619 between inputs 613, 615 and functionality at the distal end 610, internal tubes may or not be directly connected to inputs 613, 615 or distal end outputs 621, 623. Rather, tubes 617, 619 may connect to fluid pathways within the proximal end 605 that are, in turn, connected to inputs 613, 615; and tubes 617, 619 may likewise connect to fluid pathways within distal end 610 that are, in turn, connected to outputs 621, 623.

In an embodiment, tubes 617, 619 may be completely enclosed within the respective outer housings 605a, 608a, 610a provided by the proximal end 605, the coupler 608, and the distal end 610. That is, the tubing 617, 619 may have a substantially clear movement path 630 that extends substantially axially about the circumference within handpiece 600 from the proximal end 605 to the distal end.

To allow for movement of tubing 617, 619 about path 630 during the axial rotation allowed by coupler 608, the tubing 617, 619 is formed of a flexible and/or substantially elastic composition, such as silicon or the like. This flexibility allows the tubing to move while a surgeon rotates the distal end 610 independent of the proximal end 605. Axial rotation up to or beyond about 350 degrees is provided by having the flexible silicon tubes inside the handpiece 600 twist about the center axis of the handpiece 600.

Needless to say, other lines or tubing entering proximal end 605 may also be flexibly provided. By way of non-limiting example, power line 633 may also be internally flexible within the handpiece 600 to allow for axial twisting about path 630.

Also illustrated in FIG. 6A is at least one tubing/cord manager 625. Tubing/cord management 625 may positionally maintain at least aspects of cords/tubes 617, 619, such as against the inner surface of either or both of housings 605a, 610a, while also allowing freedom to twist about the center axis by tubing 617, 619 proximate to coupler 608.

Moreover, internal couplings 650, 652, 654 of tubing/cords within handpiece along path 630 may be positioned and/or angled to account for the twisting of tubes 617, 619 and/or cord within path. By way of example, internal couplings 650, 652, 654 may comprise connectivity to tubes 617, 619 and/or cords that is angled perpendicularly to the center axis of handpiece 600. This angled connectivity may decrease the alignment of the pulling force as tubing 617, 619 (and/or cords) twists with the angle of connection of tubing 617, 619 and cords to internal couplings 650, 652, 654. Obviously, this will decrease breakdowns and failures of the coupling, and improve the lifetimes of hardware associated with the couplings 650, 652, 654 (shown with greater particularity in FIG. 6B).

The internal structures needed for activation of ultrasound for the phacoemulsification handpiece, e.g. piezoelectric crystals, may be located in the distal end, the proximal end, or both. In an embodiment, if there are more than two segments, the various internal structures may be located in any segment or in multiple segments.

In addition, one or more O-ring gaskets may be used on the proximal and distal segments to create a seal between the parts and assist with the disclosed rotation. In an additional embodiment, bearings or tubing may be used alone or in combination with another similar feature, e.g., O-ring, bearing, tubing, etc., for creating a seal between the various parts of the handpiece to prevent fluids from entering or exiting the handpiece at these locations.

In an embodiment, the distal segment and proximal segment may be separable to replace the distal segment with another distal segment that may have the same or different needle and/or sleeve. In addition, the proximal segment may be designed to be serializable, and thus reusable. The distal segment may be designed to be disposable or reusable.

In an embodiment, the one or more segments may be of any material suitable for the handpiece application. The segments may be titanium, plastic, rubber, or any similar material. Each segment may have its own material type or the same material type as another segment.

Although the disclosure has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure.

What is claimed is:

1. A phacoemulsification handpiece comprising:
   a first segment having a longitudinal axis, and a first end and a second end, wherein at least aspiration, irrigation and power inputs enter the first end;
   a second segment along the longitudinal axis and comprising, at a distalmost portion thereof from the first segment, a needle powered by the power input, an aspiration output, and an irrigation output;
   a rotating coupler capable of coupling the second end of the first segment and the second segment to enable independent axial rotation about the longitudinal axis of the first segment freely from the second segment; and
   a plurality of flexible tubing passing substantially along the longitudinal axis within both the first segment and the second segment, wherein at least a first flexible tube of the plurality provides fluidic communication between the aspiration input and the aspiration output, and at least a second flexible tube of the plurality provides fluidic communication between the irrigation input and the irrigation output;
   wherein during axial rotation of the second segment relative to the first segment, the plurality of flexible tubing flexes within the first and second segments and within the rotating coupler so as to twist about the longitudinal axis.

2. The handpiece of claim 1, wherein each one of the plurality of flexible tubing comprise multiple distinct pieces of tubing.

3. The handpiece of claim 1, further comprising a tube cavity within the first segment, the second segment, and the coupler, wherein the passing of the plurality of flexible tubing substantially along the longitudinal axis within both the first segment and the second segment comprises passing through the tube cavity.

4. The handpiece of claim 1, wherein the plurality of flexible tubing is substantially elastic.

5. The handpiece of claim 1, wherein the axial rotation is unconstrained by the plurality of flexible tubing over at least 90 degrees of relative independent axial rotation.

6. The handpiece of claim 1, wherein each one of the plurality of flexible tubes comprise silicon tubes.

7. The handpiece of claim 1, further comprising a flexible power cable substantially commensurate with the plurality of flexible tubing from the power input to a power supply for the needle.

8. The handpiece of claim 1, further comprising a tubing manager that at least partially positionally maintains the plurality of flexible tubing.

9. The handpiece of claim 1, further comprising a plurality of internal couplings for at least the plurality of flexible tubing having an angular orientation to de-stress the plurality of flexible tubing at the internal coupling upon the axial rotation.

10. The handpiece of claim 1, wherein the needle is actuated by piezoelectric crystals located
   in the second segment and powered from the power input.

11. The handpiece of claim 1, further comprising a first seal between the first segment and the rotating coupler.

12. The handpiece of claim 11, wherein the first seal comprises an o-ring gasket.

13. The handpiece of claim 1, further comprising a second seal between the second segment and the rotating coupler.

14. The handpiece of claim 13, wherein the second seal comprises an o-ring gasket.

15. The handpiece of claim 1, wherein the first segment is separable from the rotating coupler.

16. The handpiece of claim 1, wherein the second segment is separable from the rotating coupler.

17. The handpiece of claim 16, wherein the separability of the second segment enables a change to at least the needle.

18. The handpiece of claim 1, wherein the first segment is sterilizable.

19. The handpiece of claim 1, wherein the second segment is disposable.

20. The handpiece of claim 1, wherein the plurality of flexible tubing is capable of both flexation and rotation.

* * * * *